(12) United States Patent
Kim

(10) Patent No.: US 12,374,436 B2
(45) Date of Patent: Jul. 29, 2025

(54) METHOD, APPARATUS, AND COMPUTER-READABLE RECORDING MEDIUM FOR PROVIDING EXERCISE CONTENTS BASED ON MOTION RECOGNITION FOR MOVEMENT OF BUST AREA

(71) Applicant: Beyondmedicine Co., Ltd., Seoul (KR)

(72) Inventor: Dae Hyun Kim, Seoul (KR)

(73) Assignee: Beyondmedicine Co., Ltd., Seoul (KR)

( * ) Notice: Subject to any disclaimer, the term of this patent is extended or adjusted under 35 U.S.C. 154(b) by 362 days.

(21) Appl. No.: 18/102,755

(22) Filed: Jan. 29, 2023

(65) Prior Publication Data

US 2024/0212820 A1 Jun. 27, 2024

(30) Foreign Application Priority Data

Dec. 22, 2022 (KR) .......................... 10-2022-0181307

(51) Int. Cl.
*G16H 20/30* (2018.01)
*A63B 71/06* (2006.01)

(52) U.S. Cl.
CPC ......... *G16H 20/30* (2018.01); *A63B 71/0619* (2013.01)

(58) Field of Classification Search
CPC .... G16H 20/30; G16H 30/40; A63B 71/0619; A61B 5/1116; A61B 5/1123; G06T 7/20; G09B 19/0038
See application file for complete search history.

(56) References Cited

U.S. PATENT DOCUMENTS

| | | | |
|---|---|---|---|
| 2014/0200470 A1* | 7/2014 | Puolakanaho | G16H 20/30 600/509 |
| 2014/0336947 A1* | 11/2014 | Walke | A61B 5/6898 702/19 |
| 2021/0259330 A1* | 8/2021 | Chahal | A41C 3/0057 |
| 2022/0183592 A1* | 6/2022 | Oliveira Santos | A61B 5/684 |

* cited by examiner

*Primary Examiner* — Garrett K Atkinson

(57) ABSTRACT

A method for providing exercise contents based on motion recognition for a movement of a bust area of a user, includes: an exercise content providing step of outputting, through a user interface executed in a user terminal, exercise contents including multimedia contents; an exercise data extracting step of extracting, from recognized motion data, exercise data including identification information about a body area of the user subject to exercise and numerical information indicating a quantitative value of the exercise by recognizing a user's motion using image data about the target area captured by a capturing unit of the user terminal; and a result data calculating step of calculating result data, which is quantitative data about body improvement of the user by using the exercise data extracted in the exercise data extracting step and user status data including health status information and body specification information of the user.

10 Claims, 9 Drawing Sheets

[FIG. 1]
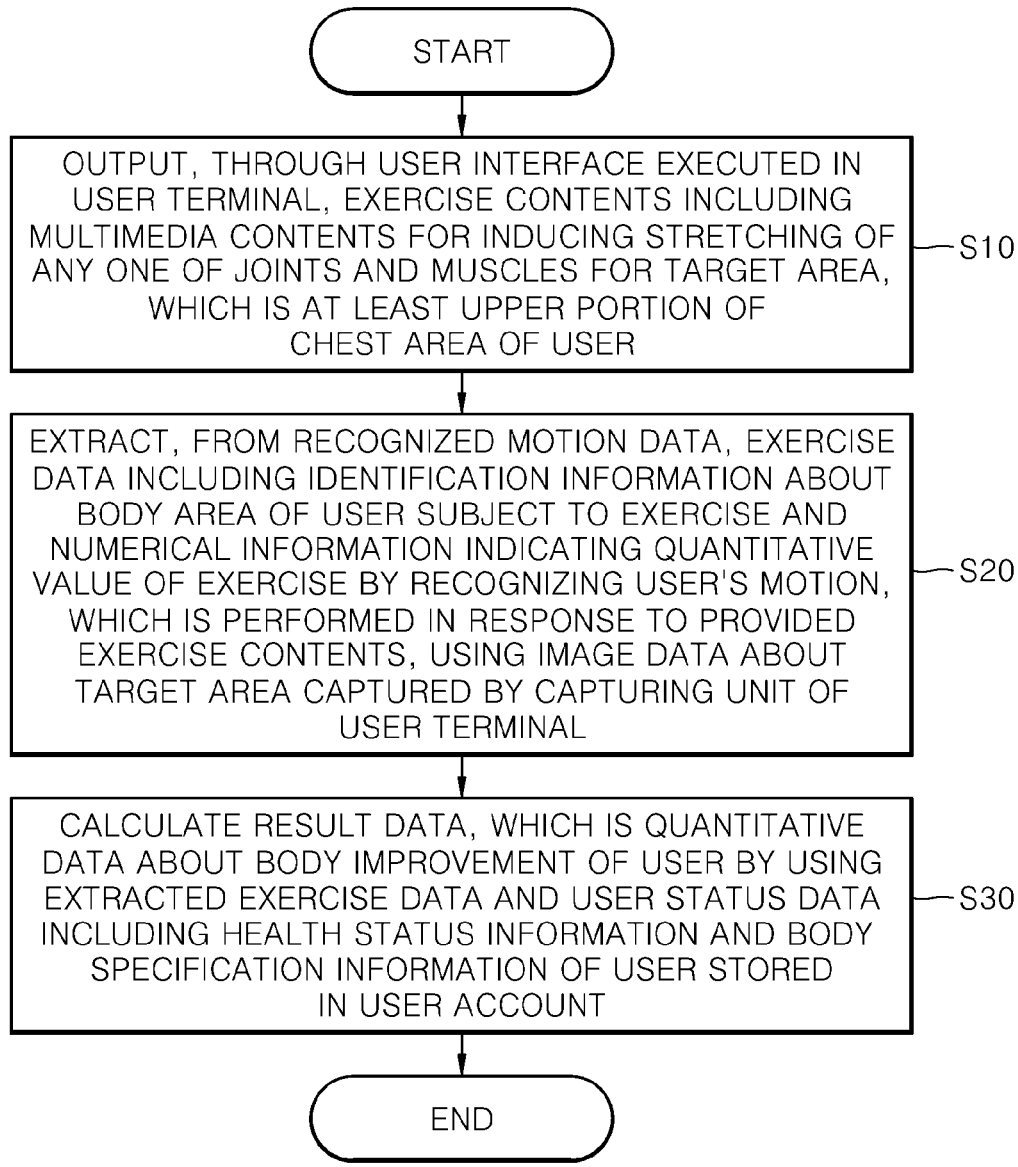

[FIG. 2]
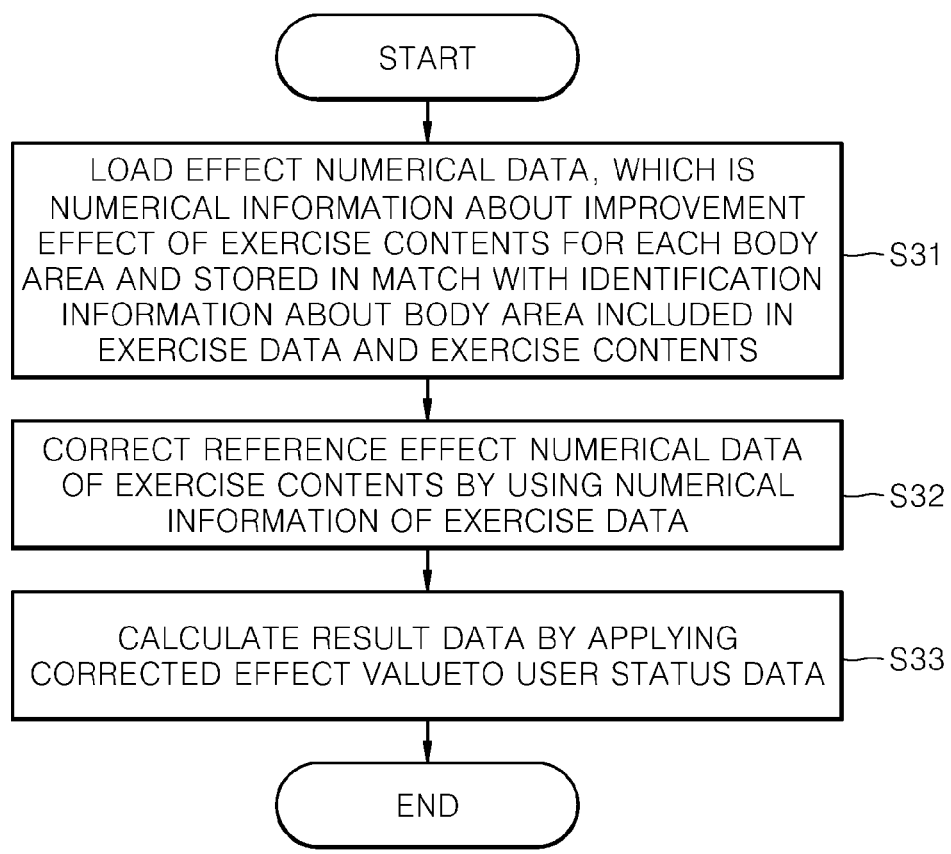

[FIG. 3]
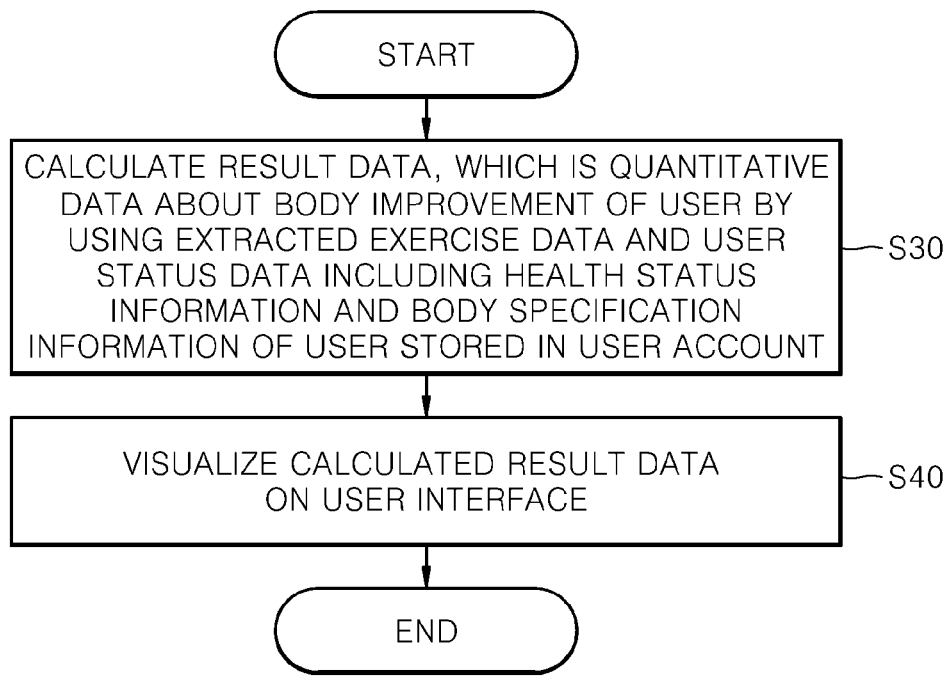

[FIG. 4]
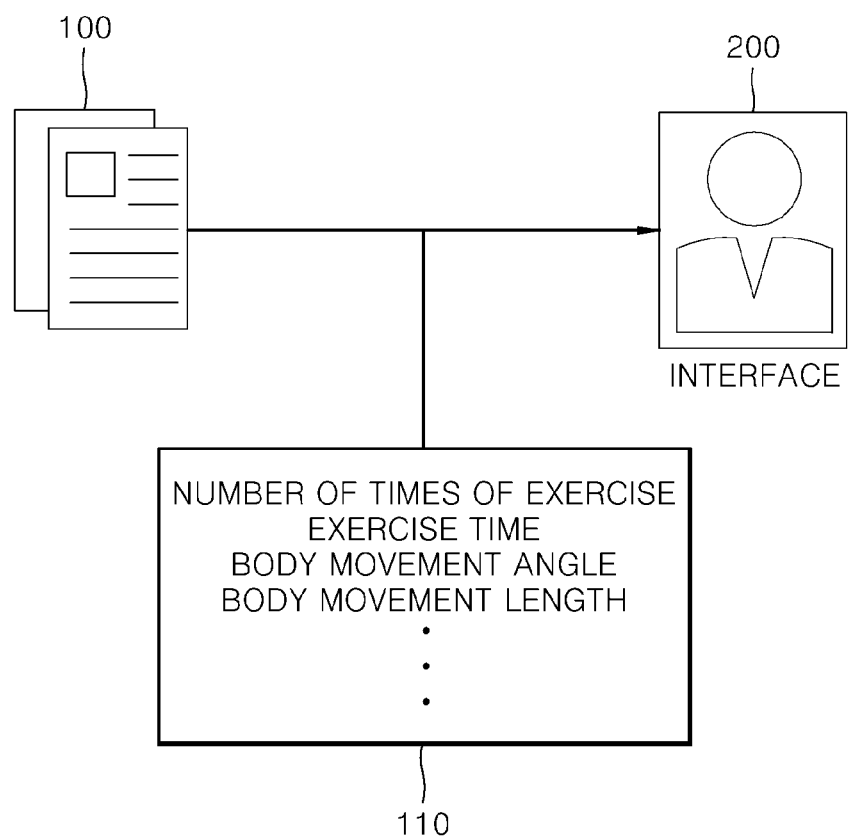

[FIG. 5]
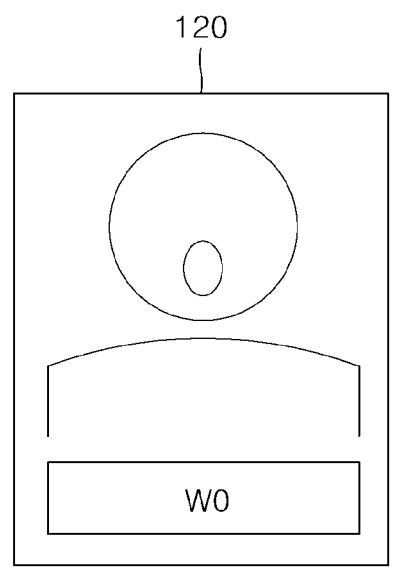

【FIG. 6】
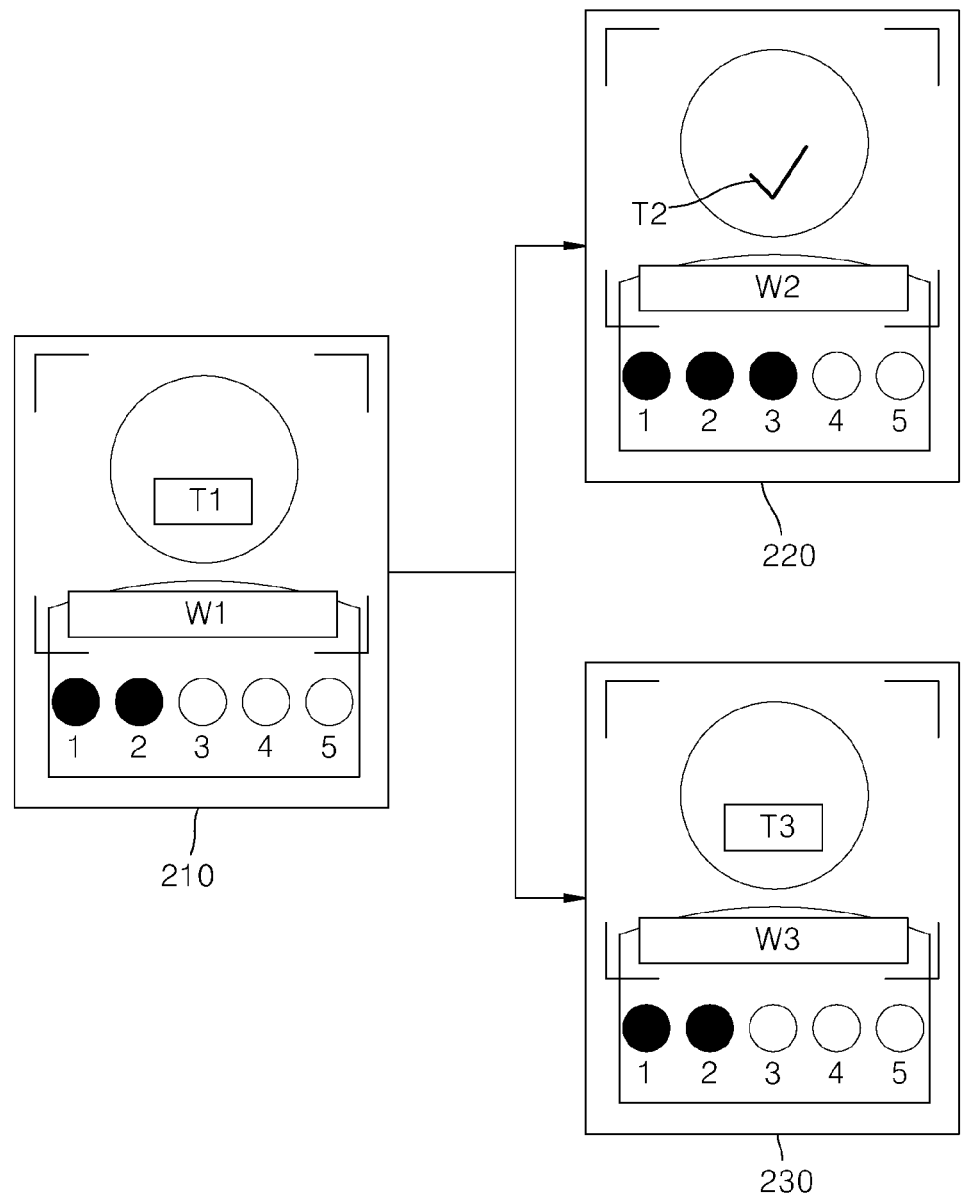

[FIG. 7]
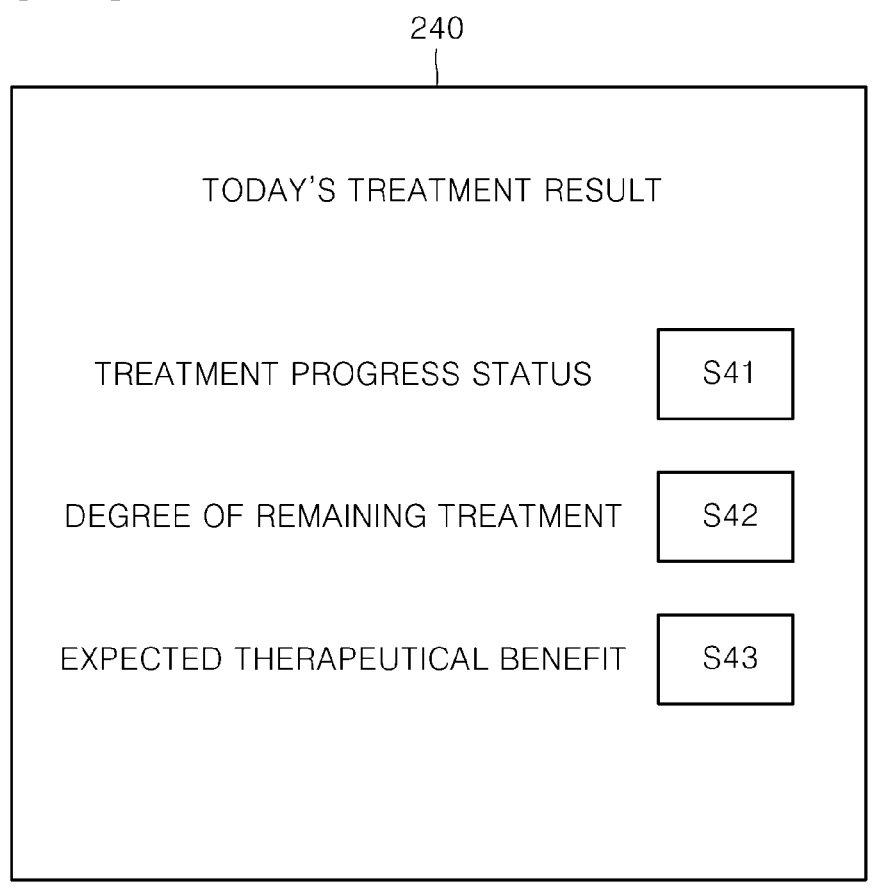

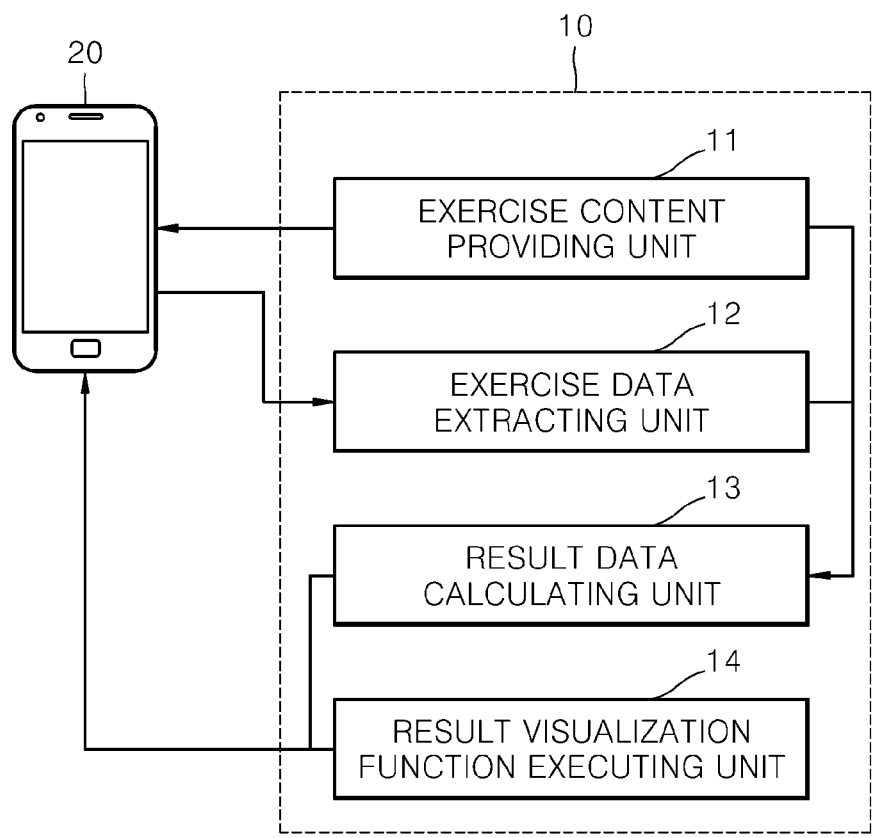

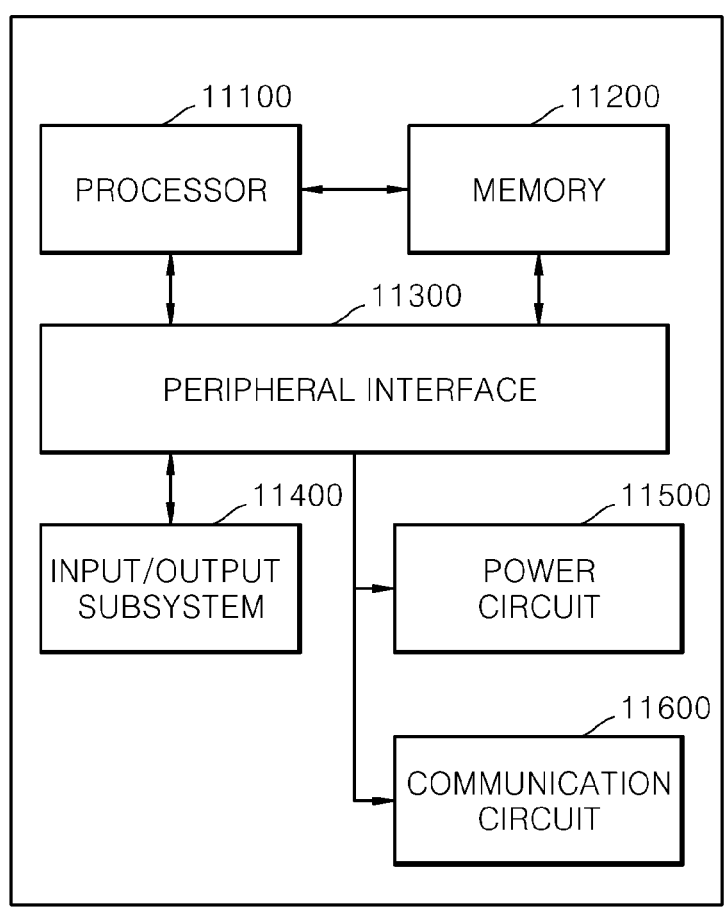

METHOD, APPARATUS, AND COMPUTER-READABLE RECORDING MEDIUM FOR PROVIDING EXERCISE CONTENTS BASED ON MOTION RECOGNITION FOR MOVEMENT OF BUST AREA

BACKGROUND OF THE INVENTION

1. Field of the Invention

The present invention relates to a technology to provide exercise contents based on motion recognition for a movement of a bust area of a user, and more specifically, to a technology to help stretching of user's face, neck, and shoulder and a symptomatic treatment related to a corresponding part by outputting, through a user interface, exercise contents for inducing stretching of any one of joints and muscles for an upper portion of a chest area of a user, and extracting exercise data from a user's motion performed in response to the exercise contents, thereby providing result data according to the extracted exercise data.

2. Description of the Related Art

Recently, a non-contact medical treatment is attracting attention to improve medical accessibility and replacing insufficient medical personnel, and simultaneously, interest in platforms for providing a non-contact medical treatment is being increased. This platform not only simply reserves the medical treatment or service or conducts the non-contact medical treatment, but also issues digital prescriptions and transmits/analyzes monitoring information about patients' health. Among the platforms, digital therapeutics are one of prescriptions using a digital DRM technology, and technologies to obtain a therapeutical benefit by providing stretching methods or physical treatment methods, and then allowing a user to perform the stretching methods or physical treatment methods by himself/herself.

However, because the digital therapeutics simply provides exercise contents until now, it is difficult to know what kind of effect the user can obtain, so that the user cannot determine whether he/she is performing exercise properly. For example, Korean Patent Application No. 10-2022-0148747 discloses a method for providing a digital treatment for rehabilitation of respiratory patients, which is a technology that provides an individual exercise program based on information about walking information of a user. However, according to the above technology, there are only target values, which are arbitrarily set, so that it is difficult to determine the absolute level of the user.

That is, the existing technologies are not suitable for outputting result values for users' status or allowing medical personnel to use the result values. For example, in order to solve such a problem, there is a need for a technology that provides result values, which can indicate how well the user exercises, rather than the target values, which are arbitrarily set, or provides result data which allows the medical personnel to determine that how well patients are receiving a given treatment. However, such a technology is insufficient.

SUMMARY OF THE INVENTION

The present invention has been devised to solve the problem as described above, and an object of the present invention is to provide a technology that provides exercise contents based on motion recognition for a movement of a bust area of a user to allow the user to exercise using a platform of digital therapeutics and allow the user to grasp his/her physical status, and provides data about exercise results to medical personnel to help the medical personnel accurately to grasp the status of a patient and make a detailed diagnosis later.

According to an embodiment of the present invention, a method for providing exercise contents based on motion recognition for a movement of a bust area of a user, which is implemented by a computing device including one or more processors and one or more memories for storing instructions executable in the processors, may include: an exercise content providing step of outputting, through a user interface executed in a user terminal, exercise contents including multimedia contents for inducing stretching of any one of joints and muscles for a target area, which is at least an upper portion of a chest area of a user; an exercise data extracting step of extracting, from recognized motion data, exercise data including identification information about a body area of the user subject to exercise and numerical information indicating a quantitative value of the exercise by recognizing a user's motion, which is performed in response to the exercise contents provided through the exercise content providing step, using image data about the target area captured by a capturing unit of the user terminal; and a result data calculating step of calculating result data, which is quantitative data about body improvement of the user by using the exercise data extracted in the exercise data extracting step and user status data including health status information and body specification information of the user stored in a user account.

The exercise content providing step may preferably include outputting the exercise data extracted in the exercise data extracting p through the user interface, and the user interface may preferably output the exercise data by mapping the exercise data to a body area corresponding to the identification information about the body area included in the exercise data among areas with the image data being output in real-time, and output the numerical information included in the exercise data by mapping the numerical information to the body area.

The numerical information output to the user interface may include a number of times of exercise, an exercise time, and movement angle and length of a body.

The exercise content providing step may include outputting guide information about the exercise contents to the user interface, and the guide information may include information about a body area of the user to be subject to exercise and a target value for the numerical information.

The exercise content providing step may include outputting, through the user interface, notification information indicating an achievement of the target value by using the exercise data extracted through the exercise data extracting step, when the numerical information included in the exercise data reaches the target value.

The result data calculating step may preferably include: an effect loading step of loading effect numerical data, which is numerical information about an improvement effect of the exercise contents for each body area and stored in match with the identification information about the body area included in the exercise data and the exercise contents; an effect correcting step of correcting reference effect numerical data of the exercise contents by using the numerical information of the exercise data; and a result calculating step of calculating the result data by applying an effect value corrected by the effect correcting step to the user status data.

The method may preferably further include a result visualizing step of visualizing the result data, which is calculated through the result data calculating step, on the user interface, after the result data calculating step.

The result visualizing step may include visualizing information about an improvement rate of the user status data, which reflects the result data, as compared with the user status data before using the exercise contents.

Meanwhile, an apparatus for providing exercise contents based on motion recognition for a movement of a bust area according to an embodiment of the present invention, which is implemented by a computing device including one or more processors and one or more memories for storing instructions executable in the processors, includes: an exercise content providing unit that outputs, through a user interface executed in a user terminal, exercise contents including multimedia contents for inducing stretching of at least any one of joints and muscles for a target area, which is at least an upper portion of a chest area of a user; an exercise data extracting unit that extracts, from recognized motion data, exercise data including identification information about a body area of the user subject to exercise and numerical information indicating a quantitative value of the exercise by recognizing a user's motion, which is performed in response to the exercise contents provided through the exercise content providing unit, using image data about the target area captured by a capturing unit of the user terminal; and a result data calculating unit that calculates result data, which is quantitative data about body improvement of the user by using the exercise data extracted in the exercise data extracting unit and user status data including health status information and body specification information of the user stored in a user account.

According to the present invention, it is possible to provide a user with exercise contents for a movement of a bust area of the user. Therefore, the user can more easily use the given exercise contents by performing the provided exercise contents in accordance with the guide information, and furthermore, can manage and treat diseases related to symptoms for face, neck, and shoulder parts.

In addition, the present invention can output the image data captured by the capturing unit of the user terminal in real-time through the user interface, and display the notification information on the user interface, so that it can help the user to perform the given exercise contents in the right way.

In particular, as the result data including numerical values calculated through the above-described image data is output through the user interface, users can determine how effectively they have completed the given exercise contents, and furthermore, such result data is provided to medical personnel to grasp patients' status, so that the result data can help the medical personnel to establish a future treatment plan.

BRIEF DESCRIPTION OF THE DRAWINGS

FIGS. 1 to 3 are flowcharts of a method for providing exercise contents based on motion recognition for a movement of a bust area according to one embodiment of the present invention.

FIG. 4 is a block diagram showing provision of detailed information about exercise contents according to one embodiment of the present invention.

FIG. 5 is an example of a screen a user interface that outputs guide information according to one embodiment of the present invention.

FIG. 6 is an example of a screen of the user interface that outputs notification information etc. according to one embodiment of the present invention.

FIG. 7 is an example of a screen for visualizing information about an improvement rate of user status data according to one embodiment of the present invention.

FIG. 8 is a block diagram of a configuration of an apparatus for providing exercise contents based on motion recognition for a movement of a bust area according to one embodiment of the present invention.

FIG. 9 is a diagram showing an example of an internal configuration of a computing device according to one embodiment of the present invention.

DETAILED DESCRIPTION OF THE INVENTION

Hereinafter, various embodiments and/or aspects will be disclosed with reference to drawings. In the following description, multiple concrete details will be disclosed in order to help general understanding of one or more aspects for the purpose of description. However, it will be recognized by those skilled in the art that the aspect (s) can be executed without the concrete details. In the following disclosure and accompanying drawings, specific exemplary aspects of one or more aspects will be described in detail. However, the aspects are exemplary and some equivalents of various aspects may be used, and the descriptions herein are intended to include both the aspects and equivalents thereto.

It is not intended that any "embodiment", "example", "aspect", "illustration", and the like used in the specification is preferable or advantageous over any other "embodiment", "example", "aspect", "illustration", and the like.

Further, the terms "includes" and/or "including" mean that a corresponding feature/or component exists, but it should be appreciated that the terms "include" or "including" mean that presence or addition of one or more other features, components, and/or a group thereof is not excluded.

Further, terms including an ordinal number such as "first" or "second' may be used for the names of various components, not limiting the components. These expressions are used to distinguish one component from another component. For example, a first component may be referred to as a second component and vice versa without departing the scope of the present disclosure. The term "and/or" includes a combination of a plurality of related enumerated items or any of the plurality of related enumerated items.

In addition, unless otherwise defined, all terms used herein, including technical or scientific terms, have the same meaning as commonly understood by one of ordinary skill in the art to which this invention belongs. Terms such as those defined in commonly used dictionaries should be interpreted as having a meaning consistent with the contextual meaning of the related art and should not be interpreted as either ideal or overly formal in meaning unless explicitly defined in the present disclosure.

FIGS. 1 to 3 are flowcharts of a method for providing exercise contents based on motion recognition for a movement of a bust area according to one embodiment of the present invention, FIG. 4 is a block diagram showing provision of detailed information about exercise contents according to one embodiment of the present invention, FIG. 5 is an example of a screen of a user interface that outputs guide information according to each embodiment of the present invention, FIG. 6 is an example of a screen of the user interface that outputs notification information etc.

according to each embodiment of the present invention, FIG. 7 is an example of a screen for visualizing information about an improvement rate of user status data according to one embodiment of the present invention, FIG. 8 is a block diagram of a configuration of an apparatus for providing exercise contents based on motion recognition for a movement of a bust area according to each embodiment of the present invention, and FIG. 9 is a diagram showing an example of an internal configuration of a computing device according to each embodiment of the present invention. In the following description, various embodiments and components of the present invention will be described with reference to a plurality of drawings.

Referring to the drawings, first, a method for providing exercise contents based on motion recognition for a movement of a bust area according to one embodiment of the present invention (hereinafter referred to as a "method of the present invention") may be implemented by a computing device to be mentioned in description of FIG. 9, which will be described later, or each component of an apparatus 10 for providing exercise contents based on motion recognition for a movement of a bust area according to the present invention (hereinafter referred to as an "apparatus of the present invention"), which is shown in FIG. 8. That is, in relation to the computing device of FIG. 9 with the apparatus 10 of the present invention, it may be understood that the computing device includes the apparatus 10 of the present invention, the computing device of FIG. 9 and the apparatus 10 have the same configuration, or a groupware including a plurality of computing devices constitutes the apparatus 10 of the present invention.

Based on the above-described contents, as shown in FIG. 1, in performing the method of the present invention, the computing device performs an exercise content providing step S10 of outputting, through a user interface executed in a user terminal, exercise contents including multimedia contents for inducing stretching of any one of joints and muscles for a target area, which is at least an upper portion of a chest area of a user.

The target area, which is the upper portion of the chest area of the user, herein may mean a position of the user to be subject to exercise, such as a face area, a neck area, a shoulder area, a temporomandibular joint area, or an oral area.

The multimedia contents of the present invention may be provided only in video media or in the form of a combination of video and sound or a combination of images and text.

The exercise contents including the multimedia contents described herein may include, for example, a palate exercise using the tongue and a motion that induces neck joint stretching. The multimedia contents, which are provided in the form of video media included in such multimedia contents, may include exercise contents, and examples of the exercise contents may include digital therapeutics, health management applications, units for providing general exercise or stretching contents.

In addition, the exercise contents described herein may include exercises or stretching that can help a treatment of diseases related to a bust area, that is, essentially the face, neck, and shoulder parts.

The most well-known disease related to the face is facial nerve palsy, called Guanwasa, which refers to a disease in which muscles around the mouth and eyes are paralyzed and distorted to one side. Stretching and exercise methods that are good for such diseases may include massage by part, practicing mouth shapes, practicing facial expression movements, and blowing air into the cheeks.

The diseases related to the neck or shoulders include turtle neck syndrome and straight neck syndrome, which are diseases that require attention because the turtle neck syndrome and straight neck syndrome may cause neck discs in the future. In order to alleviate the diseases, it may be helpful to support the neck with hands and tilt the neck back or press the head with both hands.

Meanwhile, the digital therapeutics refer to advanced software medical devices that provide evidence-based therapeutic interventions to patients to prevent, manage, and treat medical disorders and diseases by applying a digital technology. Unlike the existing digital health products for health management, the digital therapeutics refer to medical devices that have been proven through clinical trials to treat diseases or disorders, and are recently attracting attention as a promoting technology in the healthcare field. In a situation in which a market of digital therapeutics is expected to grow gradually due to the development of the digital technology and increased interest in healthcare, it is time for Korea to provide policy support for the field of digital therapeutics. Unlike the general digital healthcare products for only health management, the digital therapeutics has a difference in that they have proven a "therapeutical benefit' through clinical trials.

In S10, the exercise contents are output through the user interface executed in the user terminal, and in this case, the user terminal may include a personal computer (PC), a laptop computer, a mobile phone, etc.

In addition, the user interface may be output in the form of a plurality of menus from the user terminal or may be output as an execution result of application or web access.

In the present invention, the expression "exercise data may be output by being mapped to a body area corresponding to the identification information" means that, for example, exercise data or numerical information about the neck may be output to the neck area, and exercise data or numerical information about the chin may be output to the chin area.

In addition, the output information includes lines, numbers, angles, etc., and may be output without limiting the shape. In particular, as in the example described above, the exercise data may be mapped to an area, which is a stretching target among body areas, to output the exercise data to the area. For example, in case of a mouth opening exercise, a separation distance between both lips may be output or an index line may be output along a boundary line of a lip area, and in case of a neck joint rotation exercise, an angle at which the neck joint is rotated may be reflected according to a real-time exercise and output while changing the angle in real-time.

In S10, the guide information may include multimedia information 120 to be performed by the user as shown in FIG. 5. For example, as shown in FIG. 5, an example of a scene that the user opens the mouth may be provided in the form of a combination of video and sound, a sentence W0 for explaining the motion may be output, and a target value for the motion may be provided together with the sentence W0.

For example, the guide information may be provided to the user by outputting, to W0, a sentence such as "put your tongue behind front teeth and open the mouth 5 cm for 3 sets of 6 seconds".

In S10, the step of outputting the exercise contents to the user interface by a capturing unit of the user terminal may include information about a body area of the user to be subject to exercise, a target time value T1, which is information for displaying a target value etc. to the user, information W1 for guiding exercise motions, precautions during the motions, as shown in an interface configuration screen 210 of FIG. 6.

For example, sentences such as "stop counting when you are going out of the frame.", "put the mouth open 5 cm.", "hold the motion for 10 seconds.", and "repeat the stretching 5 times" may be changed and output to W1 step by step, so that the user can perform the contents in sequence. In addition, for example, when the number "6.0" is output to T1, it may notify the user that 6 seconds are left.

In addition, with reference to FIG. 4, numerical information 110 output from a user interface 200 in S10 may include the number of times of exercise, movement angle and length of the body, etc., and may be changed as the user exercise in accordance with the guide information 100 of the exercise contents.

For example, when the user performs oral stretching exercise of opening the mouth after putting the tongue on the palate 3 times for 5 seconds, length information indicating how many cm the user opened his/her mouth and information about the exercise time of 5 seconds and the number of times of exercise of 3 times may be output to the user interface 200. When the user performs stretching exercise of tilting the head 2 times for 10 seconds, angle information indicating how many degrees the user tilts his/her head and information about the exercise time of 10 seconds and the number of times of 2 times may be output to the user interface 200.

As shown in FIG. 6, when the user performs the correct motion according to the guide information given in the interface configuration screen 210, it may be notified by outputting reduction in time of T1 through the user interface, and notification information T2 indicating that a target value has been achieved may be output as a symbol or the like through an interface notification screen 220.

For example, when the target value of T1 is 6 seconds, 6 seconds may be reduced to 0 seconds if the user performs the motion correctly.

Further, a sentence such as "you move well in match with the target angle" or "2 sets are left. Please continue the stretching" may be output to W2 as notification information in the same set, and a sentence such as "the motion is complete. Proceed to next stretching" may be output to W2 as notification information when one set has been completed.

If the user cannot perform the motion correctly according to the guide information given in the interface configuration screen 210, T3 may be reset to an initial set time value like an interface retry notification screen 230, a sentence such as "hold the correct posture." may be output to W3 as notification information, and a screen color of the interface retry notification screen 230 may be shown in red. The notification information includes all concepts thereof.

Meanwhile, a motion recognition technology refers to a technology that controls a movement or position of a specific object using various sensors, and in this case, the sensor serves to recognize a movement of user's body and interact with various devices. The motion recognition technology may recognize motions from simple reactions, such as monitoring the movement of objects, to delicate facial expressions of people.

The motion recognition technology as described herein refers to motion recognition using a general camera, and may separate and recognize an image based on information about the contour or pattern of objects that are already known, like a facial recognition technology that finds the face in a picture. This method may be processed through a basic camera mounted in a smartphone, a tablet computer, and a laptop computer, and may be operated with only software without additional hardware, so that it may be an advantageous technology in terms of unit cost of parts.

After or during S10, the computing device recognizes, for example, a user's motion captured through the capturing unit of the user terminal by using image data about the target area. Thereafter, an exercise data extracting step S20 of extracting, from the recognized motion data, exercise data indicating identification information about a body area of the user subject to exercise and a quantitative value of the exercise, is performed.

The user's motion herein is captured by, for example, a camera such as a smartphone, and may be recognized using captured image data about the target area. For example, when the user performs an exercise related to neck muscles, the corresponding exercise motion may be recognized using image data about the neck muscles captured by the camera.

Meanwhile, the identification information acquired from the present invention includes a body area of the exercise as one of areas corresponding to an upper portion of a chest area. In addition, numerical information indicating the quantitative value includes a length of the body movement while exercising, an angle of the body tilt, the number of times of exercise, etc., and may be understood as a value for a motion of the exercise.

In S20, assuming that for example, an exercise for a neck muscle area is performed for 3 sets of 5 times, in a process for extracting the exercise data, identification information about the neck muscle area and data that a quantitative value of the corresponding area subject to exercise is 3 sets of 5 times, may be extracted from the recognized motion data.

When S20 has been completed, the computing device performs a result data calculating step S30 of calculating result data, which is quantitative data about body improvement of the user by using the exercise data extracted in the exercise data extracting step and the user status data.

The user status data is stored in the user account and may include health status information and body specification information of the user, for example, information about whether the user is healthy or has a disease and information about user's height, weight, gender, age, etc.

Meanwhile, in S30, since the purpose of the exercise contents is to improve the body area of the user or relieve symptoms of diseases, in the present invention, a detailed process as shown in FIG. 2 may be performed when performing S30 in order to achieve the main purpose of the exercise contents.

Referring to FIG. 2, in S31, the computing device loads effect numerical data about an improvement effect for each body area in order to calculate result data after extracting the exercise data and during calculation of the result data.

For example, when a motion for improving an uncomfortable neck joint refers to a first content, the first content may include a motion of stretching the neck by tilting the neck to the side, a motion of turning the shoulders, etc. In addition, information indicating that the first content has an effect of obtaining 10 points for a neck joint area and an effect of obtaining 5 points for a shoulder muscle area may be stored in the computing device.

When S31 is performed, a step S32 of correcting a value for the loaded effect numerical data by using data numerical information about the user subject to exercise is performed.

That is, S32 is a process of correcting the data by reflecting how well the user performed, in S20, the guide information about the exercise contents given in S10.

For example, assuming that the user may obtain 10 points when the user performs a motion of tilting the neck to the side 5 times, it means that a numerical value is obtained by correcting a numerical value to 8 points and reflecting the numerical value when the user performs the motion only 4 times.

In this case, the corrected effect numerical data is affected by not only the numerical information of the exercise contents of the user, but also the user status data. Therefore, as in S33, a step of calculating final result data by applying the corrected effect numerical data to the user status data may be required.

Thus, after S32, a result calculating step S33 of calculating result data using the user status data is performed.

In this case, as described above, a value of the result data refers to a value to which the user status data is applied, and for example, the user status data refers to data including all health status, body specification, etc., of the user.

S40 may be illustrated as shown in FIGS. 3 and 7, for example. That is, S40 is a step after S30, and a step of visualizing the calculated result data on a management screen 240 of the user interface.

When S40 is performed, a result of the user subject to exercise is output to the user as a data value. For example, as shown in FIG. 7, the management screen 240 provides results values for a therapeutical benefit and progress status S41 for each content, and a degree of remaining treatment and an expected therapeutical benefit S43, which can be known through S41.

In addition, it may be understood that the management screen 240 naturally contents includes for providing information about how much the user has exercised through the given exercise contents.

Through S40, the user can confirm how much effect can be obtained through the exercise contents of the user subject to exercise through visual data. This is because the final result data is a value that fluctuates according to the extent to which the user has performed the exercise contents through S10 and S20.

In addition, a result data value of S33 or S40 is provided to medical personnel together with account information about the user, so that the result data value can act as a positive function of digital therapeutics. For example, the result data value may be helpful for the medical personnel to accurately grasp a current status of the patient and treatment achievement progress without directly interviewing or treating the patient and to establish a future treatment plan. In addition, the medical personnel may use the result data value to derive recommended prescription drugs and recommended digital therapeutics information.

FIG. 8 is a block diagram of an apparatus for providing exercise contents based on motion recognition for a movement of a bust area according to one embodiment of the present invention.

Referring to FIG. 8, the apparatus 10 for providing exercise contents based on motion recognition for a movement of a bust area may include an exercise content providing unit 11, an exercise data extracting unit 12, a result data calculating unit 13, and a result visualization function executing unit 14.

According to one embodiment, the exercise content providing unit 11 may output, through a user interface 20 executed in a user terminal, exercise contents including multimedia contents for inducing stretching of at least any one of joints and muscles for a target area, which is at least an upper portion of a chest area of a user. That is, in the description described above, the exercise content providing unit 11 may be understood as a configuration of performing all functions described in S10.

According to one embodiment, the exercise data extracting unit 12 may extract, from recognized motion data, exercise data including identification information about a body area of the user subject to exercise and numerical information indicating a quantitative value of the exercise by recognizing a user's motion, which is performed in response to the exercise contents provided through the exercise content providing unit, using image data about the target area captured by the capturing unit of the user terminal; and That is, in the description described above, the exercise data extracting unit 12 may be understood as a configuration of performing all functions included in S20.

According to one embodiment, the result data calculating unit 13 may calculate result data, which is quantitative data about body improvement of the user by using the extracted exercise data and user status data including health status information and body specification information of the user stored in a user account. That is, in the description described above, the result data calculating unit 13 may be understood as a configuration of performing all functions described in S30, S31, S32, and S33.

According to one embodiment, the result visualization function executing unit 14 may visualize the calculated result data on the user interface 20. That is, in the description described above, the result visualization function executing unit 14 may be understood as a configuration of performing all functions included in S40.

According to one embodiment, the exercise data extracting unit 12 may extract exercise data included in image data captured through the capturing unit of the user terminal when the exercise contents are output to the user interface 20.

According to one embodiment, the result data calculating unit 13 may calculate the result data, which is quantitative data about body improvement by using the extracted exercise data and the user status data.

According to one embodiment, the result visualization function executing unit 14 may output the result data calculated from the result data calculating unit 13 through the user interface 20.

FIG. 9 shows an example of an internal configuration of a computing device according to one embodiment of the present invention. In the following description, unnecessary descriptions for embodiments redundant with those of FIGS. 1 to 8 will be omitted.

As shown in FIG. 9, a computing device 10000 may at least include at least one processor 11100, a memory 11200, a peripheral interface 11300, an input/output (I/O) subsystem 11400, a power circuit 11500, and a communication circuit 11600. In this case, the computing device 10000 may correspond to a user terminal A connected to a tactile interface device or correspond to the above-described computing device B.

The memory 11200 may include, for example, a high-speed random access memory, a magnetic disk, an SRAM, a DRAM, a ROM, a flash memory, or a non-volatile memory. The memory 11200 may include a software module, an instruction set, or other various data necessary for the operation of the computing device 10000.

In this case, access to the memory 11200 from other components of the processor 11100 or the peripheral interface 11300, may be controlled by the processor 11100.

The peripheral interface 11300 may combine an input and/or output peripheral device of the computing device 10000 to the processor 11100 and the memory 11200. The processor 11100 may execute the software module or the instruction set stored in the memory 11200, thereby performing various functions for the computing device 10000 and processing data.

The input/output subsystem 11400 may combine various input/output peripheral devices to the peripheral interface 11300. For example, the input/output subsystem 11400 may include a controller for combining the peripheral device such as monitor, keyboard, mouse, printer, or a touch screen or sensor, if needed, to the peripheral interface 11300. According to another aspect, the input/output peripheral devices may be combined to the peripheral interface 11300 without passing through the input/output subsystem 11400.

The power circuit 11500 may provide power to all or a portion of the components of the terminal. For example, the power circuit 11500 may include a power failure detection circuit, a power converter or inverter, a power status indicator, a power failure detection circuit, a power converter or inverter, a power status indicator, or arbitrary other components for generating, managing, or distributing power.

The communication circuit 11600 may use at least one external port to enable communication with other computing devices.

Alternatively, as described above, the communication circuit 11600 may include an RF circuit, if needed, to transmit and receive an RF signal, also known as an electromagnetic signal, thereby enabling communication with other computing devices.

The above embodiment of FIG. 9 is merely an example of the computing device 10000, and the computing device 11000 may have a configuration or arrangement in which some components shown in FIG. 9 are omitted, additional components not shown in FIG. 9 are further provided, or at least two components are combined. For example, a computing device for a communication terminal in a mobile environment may further include a touch screen, a sensor or the like, in addition to the components shown in FIG. 9. The communication circuit 11600 may include a circuit for RF communication of various communication schemes (such as WiFi, 3G, LTE, Bluetooth, NFC, and Zigbee). The components that may be included in the computing device 10000 may be implemented by hardware, software, or a combination of both hardware and software which include at least one integrated circuit specialized in a signal processing or an application.

The methods according to the embodiments of the present invention may be implemented in the form of program instructions to be executed through various computing devices so as to be recorded in a computer-readable medium. In particular, a program according to the embodiment of the present invention may be configured as a PC-based program or an application dedicated to a mobile terminal. The application to which the present invention is applied may be installed in a user terminal through a file provided by a file distribution system. For example, a file distribution system may include a file transmission unit (not shown) that transmits the file according to the request of the user terminal.

The above-described device may be implemented by hardware components, software components, and/or a combination of hardware components and software components. For example, the devices and components described in the embodiments may be implemented by using at least one general purpose computer or special purpose computer such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing device may execute an operating system (OS) and at least one software application executed on the operating system. In addition, the processing device may access, store, manipulate, process, and create data in response to the execution of the software. For the further understanding, in some cases, one processing device may be used, however, those skilled in the art will be appreciated that the processing device may include a plurality of processing elements and/or a plurality of types of processing elements. For example, the processing device may include a plurality of processors or one processor and one controller. In addition, other processing configurations, such as a parallel processor, are also possible.

The software may include a computer program, a code, an instruction, or a combination of at least one thereof, may configure the processing device to operate as desired, or may instruct the processing device independently or collectively. In order to be interpreted by the processor or to provide instructions or data to the processor, the software and/or data may be permanently or temporarily embodied in any type of machine, component, physical device, virtual equipment, and computer storage medium or device. The software may be distributed over computing devices connected to networks, so as to be stored or executed in a distributed manner. The software and data may be stored in at least one computer-readable recording medium.

The above-described embodiments of the present invention may be recorded in computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts. Examples of computer-readable recording media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention, or vice versa.

While this disclosure includes specific examples, it will be apparent to one of ordinary skill in the art that various changes in form and details may be made in these examples without departing from the spirit and scope of the claims and their equivalents. Suitable results may be achieved if the described techniques are performed in a different order, and/or if components in a described system, architecture, device, or circuit are combined in a different manner, and/or replaced or supplemented by other components or their equivalents. Therefore, other implementations, other embodiments, and equivalents of the claims are within the scope of the following claims.

What is claimed is:

1. A method for providing exercise contents based on motion recognition for a movement of a bust area, which is implemented by a computing device including one or more processors and one or more memories for storing instructions executable in the processors, the method comprising:

an exercise content providing step of outputting, through a user interface executed in a user terminal, exercise contents including multimedia contents for inducing stretching of any one of joints and muscles for a target area, which is at least an upper portion of a chest area of a user;

an exercise data extracting step of extracting, from recognized motion data, exercise data including identification information about a body area of the user subject to exercise and numerical information indicating a quantitative value of the exercise by recognizing a user's motion, which is performed in response to the exercise contents provided through the exercise content providing step, using image data about the target area captured by a capturing unit of the user terminal; and a result data calculating step of calculating result data, which is quantitative data about body improvement of the user by using the exercise data extracted in the exercise data extracting step and user status data including health status information and body specification information of the user stored in a user account.

2. The method of claim 1, wherein the exercise content providing step includes outputting the exercise data extracted in the exercise data extracting step through the user interface, and the user interface outputs the exercise data by mapping the exercise data to a body area corresponding to the identification information about the body area included in the exercise data among areas with the image data being output in real-time, and outputs the numerical information included in the exercise data by mapping the numerical information to the body area.

3. The method of claim 2, wherein the numerical information output to the user interface includes a number of times of exercise, an exercise time, and movement angle and length of a body.

4. The method of claim 2, wherein the exercise content providing step includes outputting guide information about the exercise contents to the user interface, and the guide information includes information about a body area of the user to be subject to exercise and a target value for the numerical information.

5. The method of claim 4, wherein the exercise content providing step includes outputting, through the user interface, notification information indicating an achievement of the target value by using the exercise data extracted through the exercise data extracting step, when the numerical information included in the exercise data reaches the target value.

6. The method of claim 1, wherein the result data calculating step includes:

an effect loading step of loading effect numerical data, which is numerical information about an improvement effect of the exercise contents for each body area and stored in match with the identification information about the body area included in the exercise data and the exercise contents;

an effect correcting step of correcting reference effect numerical data of the exercise contents by using the numerical information of the exercise data; and a result calculating step of calculating the result data by applying an effect value corrected by the effect correcting step to the user status data.

7. The method of claim 1, further comprising a result visualizing step of visualizing the result data, which is calculated through the result data calculating step, on the user interface, after the result data calculating step.

8. The method of claim 7, wherein the result visualizing step includes visualizing information about an improvement rate of the user status data, which reflects the result data, as compared with the user status data before using the exercise contents.

9. An apparatus for providing exercise contents based on motion recognition for a movement of a bust area, which is implemented by a computing device including one or more processors and one or more memories for storing instructions executable in the processors, the apparatus comprising:

an exercise content providing unit that outputs, through a user interface executed in a user terminal, exercise contents including multimedia contents for inducing stretching of at least any one of joints and muscles for a target area, which is at least an upper portion of a chest area of a user;

an exercise data extracting unit that extracts, from recognized motion data, exercise data including identification information about a body area of the user subject to exercise and numerical information indicating a quantitative value of the exercise by recognizing a user's motion, which is performed in response to the exercise contents provided through the exercise content providing unit, using image data about the target area captured by a capturing unit of the user terminal; and a result data calculating unit that calculates result data, which is quantitative data about body improvement of the user by using the exercise data extracted in the exercise data extracting unit and user status data including health status information and body specification information of the user stored in a user account.

10. A computer-readable recording medium that stores instructions for allowing a computing device to perform the following steps, wherein the steps comprise:

an exercise content providing step of outputting, through a user interface executed in a user terminal, exercise contents including multimedia contents for inducing stretching of any one of joints and muscles for a target area, which is at least an upper portion of a chest area of a user;

an exercise data extracting step of extracting, from recognized motion data, exercise data including identification information about a body area of the user subject to exercise and numerical information indicating a quantitative value of the exercise by recognizing a user's motion, which is performed in response to the exercise contents provided through the exercise content providing step, using image data about the target area captured by a capturing unit of the user terminal; and a result data calculating step of calculating result data, which is quantitative data about body improvement of the user by using the exercise data extracted in the exercise data extracting step and user status data including health status information and body specification information of the user stored in a user account.

* * * * *